(12) United States Patent
Aquino et al.

(10) Patent No.: US 7,319,172 B2
(45) Date of Patent: Jan. 15, 2008

(54) PROCESS FOR THE PREPARATION OF METHYLHEPTENONE

(75) Inventors: Fabrice Aquino, Reiningue (FR); Werner Bonrath, Freiburg (DE); Aljosa Crevatin, Trieste (IT)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/588,035

(22) PCT Filed: Jan. 27, 2005

(86) PCT No.: PCT/EP2005/000795

§ 371 (c)(1),
(2), (4) Date: Feb. 23, 2007

(87) PCT Pub. No.: WO2005/075400

PCT Pub. Date: Aug. 18, 2005

(65) Prior Publication Data

US 2007/0161823 A1 Jul. 12, 2007

(30) Foreign Application Priority Data

Feb. 4, 2004 (EP) .................................. 04002422

(51) Int. Cl.
*C07C 45/37* (2006.01)
(52) U.S. Cl. ...................................... 568/403; 568/404
(58) Field of Classification Search ................ 568/403, 568/404
See application file for complete search history.

(56) References Cited

U.S. PATENT DOCUMENTS 5,886,196 A * 3/1999 Furbringer .................. 549/213
6,034,279 A * 3/2000 Kashammer et al. ....... 568/391
6,700,002 B2 * 3/2004 Bonrath et al. ............. 549/411

* cited by examiner

*Primary Examiner*—Sikarl A. Witherspoon
(74) *Attorney, Agent, or Firm*—Nixon & Vanderhye P.C.

(57) ABSTRACT

Methylheptenone (2-methyl-2-hepten-6-one) is prepared by reacting 2-methyl-3-buten-2-ol with isopropenyl methyl ether in the presence of hydrogen tris(oxalato)phosphate or hydrogen bis(oxalato)borate.

10 Claims, No Drawings

PROCESS FOR THE PREPARATION OF METHYLHEPTENONE

This application is the U.S. national phase of international application PCT/EP2005/000795 filed 27 Jan. 2005 which designated the U.S. and claims benefit of EP 04002422.6, dated 4 Feb. 2004, the entire content of which is hereby incorporated by reference.

The present invention relates to a novel process for the preparation of 2-methyl-2-hepten-6one, hereinafter referred to also as methylheptenone. It is known to prepare methylheptenone by reaction of 2-methyl-3-buten-2-ol with isopropenyl methyl ether in the presence of catalysts, e.g. phosphoric acid, see DE 1 193 490 or organic phosphates or phosphinates, see DE 196 49 564.

It has been found that hydrogen bis(oxalato)borate and, particularly, hydrogen tris(oxalato)phosphate are especially well suited to catalyze the reaction. Accordingly, the present invention is concerned with a process for the preparation of 2-methyl-2-hepten-6-one which comprises reacting 2-methyl-3-buten-2-ol with isopropenyl methyl ether in the presence of hydrogen tris(oxalato)phosphate or hydrogen bis(oxalato)borate.

The process of the present invention can be carried out at normal pressure or at elevated pressure. Preferably, the reaction is carried out at elevated pressure, e.g. at a pressure of about $10^5$ to about $20 \times 10^5$ Pascal (Pa), preferred $5 \times 10^5$ to about $15 \times 10^5$ Pa. Further, the reaction according to the present invention is preferably carried out in the absence of a solvent. The catalyst can be added in pure form or solved, preferred is the solved form in acetone or methanol. The reaction is suitably carried out at elevated temperature, e.g. at a temperature between about 373 K and about 450 K. The molar ratio of the reactants is suitably about 1:1 to 1:3, preferred is 1:2 to 1:2.5 although an excess of one of the reactants, e.g., an excess of the less expensive reactant, isopropenyl methyl ether, may be used and, if desired, be recycled after isolation of the desired reaction product from the reaction mixture.

The reaction in accordance with the present invention can be carried out batchwise or in continuous mode, e.g., in two or more serially arranged stirred tanks or in tube reactors.

The catalysts, hydrogen tris(oxalato)phosphate or hydrogen bis(oxalato)borate, may be present in the reaction mixture in amount to provide a substrate/catalyst ratio of about 1000:1 to about 100:1, preferably about 900:1 to about 300:1, based on 2-methyl-3-buten-2-ol as the substrate. Hydrogen tris(oxalato)phosphate can be prepared as disclosed in EP 1 227 089. Hydrogen bis(oxalato)borate can be prepared by the procedure described in EP 784 042.

The invention is illustrated further by the Example which follows.

EXAMPLE

The reaction was carried out using an equipment the main part was a stainless steel batch reactor (Medimex—High Pressure) with a nominal volume of 1.0 liter, an operative temperature up to 493 K and a maximum pressure of 20 bar. The reactor was equipped with a heating system (electrical heating spirals located in the jacket), a cooling system (glycol-water mixture flowing through the reactor jacket), a temperature control for the measurement of the inner reactor, jacket and cooling temperatures, and a stirrer. The reactor was coupled with a laboratory vacuum pump to remove the air from the reactor. The sampling was done via a stainless steel capillary and a thin spiraled stainless steel tube connected to the sampling flask. The catalysts were used as about 12 or 5.5 wt-% solution in methanol or 6.5 wt.-% solution in acetone (hydrogen bis(oxalato)borate), or about 12, 10 or 8 wt.-% solution in methanol or 6 wt.-% solution in acetone (hydrogen tris(oxalato)phosphate).

195 g MBE (2.22 mol), catalyst (see Table 1) and 342 g IPM (4.6 mol=2.1 eq.) were mixed and charged into the reactor. The reactor was shortly evacuated with a vacuum pump. The reaction mixture was heated up to 423 K while stirring and maintaining said temperature. Samples were taken in appropriate time intervals through the sample valve and capillary and were directly neutralized with sodium acetate. The samples were analyzed by gas chromatography (NORM %). After the reaction mixture was cooled to room temperature a sample of the remaining reaction mixture was taken (no gas phase) and analyzed by gas chromatography (NORM %).

The results are shown in Tables 1, 2 and 3 below.

TABLE 1

| Catalyst (mol-%)[1] | Catalyst solution | T (K) | Reaction time (h) | Conversion of MBE (%) | Yield MH (%) |
|---|---|---|---|---|---|
| HOB (0.15) | 5.5% methanol | 423 | 21.7 | 25.0 | 23.9 |
| HOB (0.10) | 5.5% methanol | 423 | 24 | 29.9 | 29.5 |
| HOB (0.10) | 6.5% acetone | 423 | 24 | 48.0 | 23.3 |
| HOB (0.05) | 6.5% acetone | 423 | 24 | 35.7 | 20.1 |
| HOB (0.01) | 6.5% acetone | 423 | 24 | 16.6 | 14.4 |
| HOP (0.15) | 10.0% methanol | 423 | 21.3 | 96.3 | 91.0 |
| HOP (0.15) | 11.7% methanol | 423 | 24 | 97.7 | 92.5 |
| HOP (0.15) | 11.7% methanol | 423 | 24 | 97.9 | 97.7[3] |
| HOP (0.15) | 11.7% methanol | 423 | 24 | 97.6 | 97.6[4] |
| HOP (0.12) | 10.0% methanol | 423 | 21.5 | 96.7 | 80.6 |
| HOP (0.09) | 10.0% methanol | 423 | 17 | 81.5 | 80.8 |
| HOP (0.23) | 10.0% methanol | 398 | 25 | 87.1 | 80.2 |
| HOP (0.17) | 10.0% methanol | 398 | 22 | 77.5 | 77.3[2] |
| HOP (0.15) | 6.1% acetone | 423 | 24 | 94.9 | 56.4 |

TABLE 2

| HOB (0.9) | 11.6% methanol | 423 | 24 | 50.3 | 43.2 |
|---|---|---|---|---|---|
| HOB (0.3) | 11.6% methanol | 423 | 24 | 22.0 | 20.3[4] |
| HOB (0.3) | 11.6% methanol | 423 | 24 | 28.5 | 26.1[3] |
| HOB (0.3) | 11.6% methanol | 448 | 24 | 39.2 | 37.6 |
| HOB (0.3) | 5.5% methanol | 423 | 24 | 29.8 | 28.0 |

TABLE 3

| HOP (0.14) | 6.1% acetone | 423 | 24 | 98.6 | 98.6[4] |
|---|---|---|---|---|---|
| HOP (0.30) | 11.7% methanol | 423 | 8.5 | 94.0 | 90.1 |

TABLE 3-continued

| HOP (0.30) | 7.9% methanol | 398 | 24 | 88.3 | 83.4 |
| HOP (0.30) | 11.7% methanol | 423 | 24 | 99.0 | 81.1 |

HOB: hydrogen bis(oxalato)borate;
HOP: hydrogen tris(oxalato)phosphate;
MH: methylheptenone;
MBE: 2-methyl-3-buten-2-ol;
IPM: isopropenyl methyl ether
[1]based on MBE
[2]ratio IPM/MBE = 3.3/1 (all other cases 2.1/1),
[3]ratio IPM/MBE = 2.5/1,
[4]ratio IPM/MBE = 3.0/1

What is claimed is:

1. Process for the preparation of 2-methyl-2-hepten-6-one which comprises reacting 2-methyl-3-buten-2-ol with isopropenyl methyl ether in the presence of hydrogen tris(oxalato)phosphate or hydrogen bis(oxalato)borate.

2. A process as in claim 1 wherein the reaction is carried out in the presence of hydrogen tris(oxalato)phosphate.

3. A process as in claim 1 wherein the reaction is carried out under elevated pressure.

4. A process as in claim 3 wherein the reaction is carried out at $10^5$ to $20 \times 10^5$ Pa.

5. A process as in claim 3 wherein the reaction is carried out at $5 \times 10^5$ to about $15 \times 10^5$ Pa.

6. A process as in claim 1 wherein the catalyst is present in an amount to provide a substrate/catalyst ratio of about 1000:1 to about 100:1, based on 2-methyl-3-buten-2-ol as the substrate.

7. A process as in claim 1 wherein the catalyst is present in amount to provide a substrate/catalyst ratio of about 900:1 to about 300:1, based on 2-methyl-3-buten-2-ol as the substrate.

8. A process as in claim 1 wherein the ratio of 2-methyl-3-buten-2-ol to isopropenyl methyl ether is 1:1 to 1:3.

9. A process as in claim 1 wherein the ratio of 2-methyl-3-buten-2-ol to isopropenyl methyl ether is 1:1 to 1:2.5.

10. A process as in claim 1 wherein the reaction is carried out in continuous mode.

* * * * *